United States Patent [19]
Sodickson et al.

[11] Patent Number: 5,818,044
[45] Date of Patent: *Oct. 6, 1998

[54] NON-SPECTROPHOTOMETRIC MEASUREMENT OF ANALYTE CONCENTRATIONS AND OPTICAL PROPERTIES OF OBJECTS

[75] Inventors: Lester Sodickson, Waban, Mass.; Myron J. Block, North Salem, N.H.

[73] Assignee: Optix LP, Jensen Beach, Fla.

[*] Notice: The term of this patent shall not extend beyond the expiration date of Pat. No. 5,321,265.

[21] Appl. No.: 383,293

[22] Filed: Feb. 2, 1995

Related U.S. Application Data

[60] Division of Ser. No. 130,257, Oct. 1, 1993, Pat. No. 5,434, 412, which is a continuation-in-part of Ser. No. 914,265, Jul. 15, 1992, Pat. No. 5,321,265.

[51] Int. Cl.[6] .................................................... G01N 21/35
[52] U.S. Cl. ...................................... 250/339.06; 356/405
[58] Field of Search .......................... 250/339.09, 341.1, 250/341.8, 343; 356/405

[56] References Cited

U.S. PATENT DOCUMENTS 5,321,265  6/1994  Block ........................................ 250/343

Primary Examiner—Davis L. Willis
Assistant Examiner—Richard Hanig

[57] ABSTRACT

Improvement methods and apparatus for determination of optical properties of objects have been developed. The apparatus and methods of the invention provide an analog of color perception of human vision, preferably in the near infrared region, replacing spectrophotometers and narrow band sources used in other non-invasive near infrared detection methods. A plurality of detector units are used, each covering a broad and overlapping region of the detected spectrum, paralleling color perception and colorimetry. The improvements are primarily concerned with improving the signal-to-background (or noise) ratio such that the data stream is improved. These improvements use congruent sampling, comparison of different data streams from different sample portions or filter sets, using an interrogation system with sufficient speed to allow testing of arterial blood, and using a filter with a spectral structure. In some circumstances, a neural net is used for analysis, allowing the system to learn. A novel method for background discrimination is also described.

58 Claims, 11 Drawing Sheets

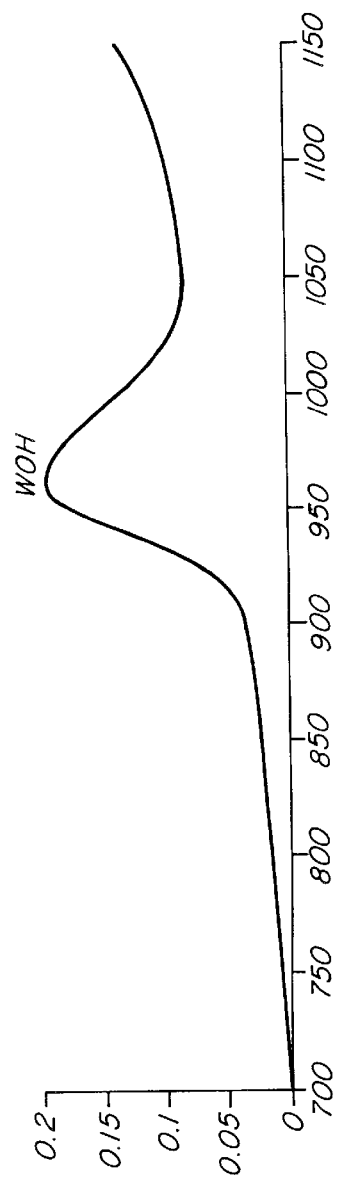
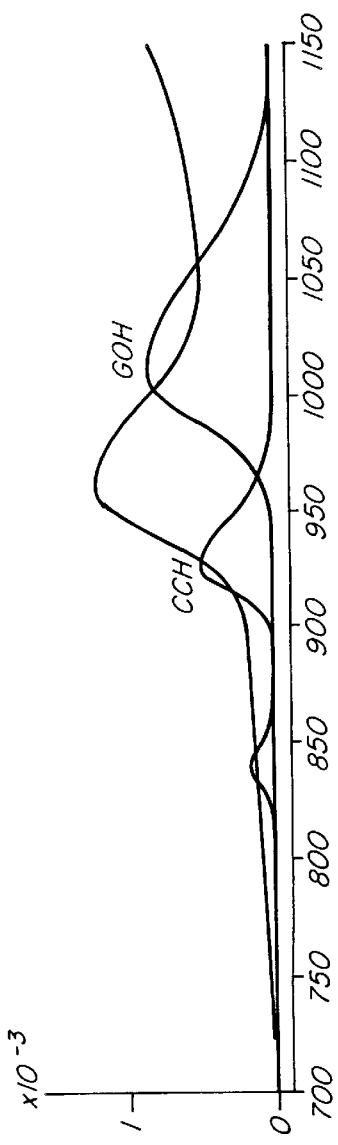

NON-SPECTROPHOTOMETRIC MEASUREMENT OF ANALYTE CONCENTRATIONS AND OPTICAL PROPERTIES OF OBJECTS

REFERENCE TO RELATED APPLICATION

This application is a divisional of application Ser. No. 08/130,257 filed on Oct. 1, 1993, now U.S. Pat. No. 5,434,412, which is a Continuation-in-Part of U.S. patent application Ser. No. 914,265, filed Jul. 15, 1992, now U.S. Pat. No. 5,321,265, entitled "Non-invasive Testing", the disclosure of which is incorporated herein by reference.

BACKGROUND OF THE INVENTION

The present invention relates to the measurement of the concentration of constituents of interest using radiation, preferably near infrared radiation. More particularly, an apparatus has been developed which utilizes a method of measuring the concentration of constituents such as glucose, alcohol, hemoglobin and its variants such as deoxyhemoglobin, myoglobin, and other reduced or substituted forms of hemoglobin or heme-group containing molecules, drugs of abuse or other clinical analytes in a non-invasive manner. Because the apparatus and method do not require a finger puncture to obtain a blood sample, they are particularly suitable for home glucose testing.

With the spread of AIDS, and the associated fear among the public and health care personnel of contracting the disease, development of testing methods that do not require invasive procedures, including the taking of blood samples, has become an important goal. Not only AIDS, but other diseases such as hepatitis may be spread through invasive procedures if adequate precautions are not taken. For example, a recent article, "Nosocomiel transmission of Hepatitis B virus associated with the use of a spring-loaded finger-stick device," *New England Journal of Medicine* 326 (11), 721–725 (1992), disclosed a hepatitis mini-epidemic in a hospital caused by the improper use of an instrument for taking blood samples. The article describes how the nurses were unintentionally transmitting hepatitis from one patient to another with the sampling device itself. This type of disease transfer is eliminated by non-invasive testing.

Effective management of diabetes has also given rise to the need for non-invasive testing instruments. Many diabetics must measure their blood glucose levels four or more times a day. Instruments currently used for in-home glucose testing require a painful finger prick to obtain a blood sample. Although the price of these instruments has dropped considerably, such testing requires the use of disposable materials that can be cumulatively costly. Further, the discomfort, inconvenience, and health risks associated with frequent puncture bleeding are considerable.

Accordingly, a number of groups have recently tried to make non-invasive instruments for measuring the concentration of various analytes, particularly blood glucose. Much of the recent development work in non-invasive testing has been exploring the use of the near infrared spectral region (700–1100 nm). This region contains the third overtones of the glucose spectrum and its use eliminates many of the water bands and other interference bands that cause potential problems for detection. However, substantially all of this work has been carried out using classic spectrophotometric methods. These methods use a set of narrow wavelength sources or scanning spectrophotometers which scan wavelength by wavelength across a broad spectrum. The data obtained with these methods are spectra which require substantial data processing to eliminate (or minimize) the background. Accordingly, the relevant papers are replete with data analysis techniques utilized in an attempt to extract the pertinent information. Examples of this type of testing include the work by Clarke, see U.S. Pat. No. 5,054,487, and the work by Rosenthal et al., see, e.g., U.S. Pat. No. 5,028,787. Although the Clarke work uses reflectance spectra and the Rosenthal work uses primarily transmission spectra, both rely on obtaining near infrared spectrophotometric data.

One problem with all such methods is that spectrophotometers were conceived primarily for accurate wavelength-by-wavelength measurement of spectral intensities. Where, as in non-invasive measurement of the concentration of glucose and other clinical materials, the analyte of interest has weak broadband spectral features and is present in a mixture containing other substances with substantially overlapping broad-band spectral structure, use of classical spectrophotometric methods employ substantial, and ultimately unsatisfactory, data analysis in an attempt to extract the desired concentration from a background of interfering signals. One basic principal of all measurement is, however, that the measurement step determines the information content of the data, and that computation or transformation adds no information. In other words, no amount of analysis can make up for the fact that the distinguishing features of the spectra of the analytes of interest are not the sharp spectral peaks of classical spectrophotometry but rather are broad and shallow structures. The analyte is identifiable not by the location of its spectral peaks, but by the global structure of its intensity versus wavelength structure. Since spectrophotometers are not designed to generate this kind of information, they are ill-suited for measurements of this type.

The spectra of the analytes of interest, consisting of a few weak low resolution features, with overlapping backgrounds, are reminiscent of the spectra of reflected, emitted, or transmitted light from colored objects in the visible. The human visual system, while an incompetent spectrophotometer, is superb at the subtlest color discrimination and identification, even under greatly varying illumination conditions. Therefore, the present invention draws on an analogy with the discrimination of colored objects by the eye, rather than classic spectrophotometric measurements, to obtain data, preferably in the infrared.

Many related but distinct approaches are possible in developing an apparatus and a method for measuring the concentration of an analyte of interest by exploiting the analogy to color perception in the visible. The primary approach is to illuminate the object with broadband radiation, the analog of white light in the visible, and to use a series of spectrally overlapping filters to detect the reflected, emitted or transmitted radiation to determine the object's relative "color." This approach is disclosed in U.S. patent application Ser. No. 914,265, the disclosure of which is incorporated herein by reference. The present application concerns modifications and improvement on the method and apparatus described therein to obtain even better data. In fact, many of these methods are useful even in classic spectrophotometric systems.

While visual perception is very complex and not completely understood, one approach for relating the concentration of an analyte to absorption or reflection in the infrared is to obtain and process the raw data as closely as possible to the known aspects of color perception, utilizing a succession of steps or processing levels. Each step provides a useful product and succeeding steps represent products of greater capability.

The first step to achieve accurate information is the simple analog of color perception using a colorimetry-like approach. Colorimetry is numerical color communication in which three dimensions are used to describe the color. It is the trivalent nature of color vision that permits color to be specified in a three dimensional space.

There presently are several such three dimensional colorimetry spaces in use. One of these spaces is the CIE 1931 (x, y)-chromaticity diagram, shown in FIG. 1b, which shows hue and saturation values. Luminosity, the third dimension, is not shown in FIG. 1b but would be in a Z-direction. FIG. 1a shows the standard observed spectral responses used to generate FIG. 1b.

Another colorimetric space, described in terms of hue, chroma, and value, is shown in FIG. 2. This solid can be described as the three numerical values which can specify any perceived color.

It is important to note that although it is convenient to describe color in terms of colorimetry, this is not true color perception which is much more complex. However, colorimetry is useful for color matching under specific conditions. An analog of colorimetry, particularly one in the infrared region, would show similar usefulness in determining analyte concentration.

There are commercially available colorimeters in the visible for measuring tristimulus values in terms of luminosity, hue and saturation, yielding numerical values such as are illustrated by FIG. 1. Briefly, these calorimeters use three detectors, with each detector input being filtered with a different filter function. Each of the filter functions and detector responses are chosen to be similar to the three absorption spectra of the pigments of the three color receptive cones of the human retina. It appears that no one other than the present inventors have previously used, or even considered the use, of an analog of color perception for wavelength expanded colorimetry for concentration measurements or even applied the method of colorimetry to infrared measurements as described herein.

In addition to non-invasive blood measurements for constituents like glucose, the system could replace present pulse oximeters. Non-invasive measurement of arterial oxygen saturation by pulse oximetry is widely acknowledged to be one of the most important technological advances in clinical patient monitoring. Pulse oximeters measure differences in the visible and near infrared absorption spectra of fully oxygenated and reduced hemoglobin in arterial blood. Unlike clinical blood gas analyzers, which require a sample of blood from the patient and can only provide intermittent measurement of patient oxygenation, pulse oximetry provide continuous, and instantaneous, measurement of blood oxygen levels.

However, current commercial oximeters, and their algorithms are inaccurate under conditions of low pulse pressure and/or low oxygen saturation. These severe conditions are observed in the normal unborn fetus or where the features of interest are broad. Unlike the transmission sampling of the commercial oximeters, space limitations associated with the fetus require that the spectral data be obtained by reflectance sampling. It has been suggested that a new analysis technique using multivariate calibration methods can improve the precision, accuracy and reliability of quantitative spectral analysis. Even these techniques are limited by the type of input data.

The apparatus and methods of U.S. patent application Ser. No. 914,265 solves this problem by providing infrared analogs of colorimetry. While the data provided is better than that from spectrophotometers, signal-to-background can always be improved, thereby providing even greater sensitivity.

Accordingly, an object of the invention is to provide an apparatus which provides an improved measure of the concentration of a constituent of interest or a determination of optical properties of an object in a sample using an analog of color perception.

Another object of the invention is to provide an improved method of accurately, inexpensively, and quickly measuring the concentration of clinical analytes in a non-invasive manner using an analog of colorimetric analysis.

A further object of the invention is to provide an improved apparatus for, and a method of, non-invasive concentration measurements using the analogs of colorimetry and color perception that allows for convenient sample insertion and removal and is not responsive to radiation from extraneous sources.

A still further object of the invention is to provide an apparatus for and a method of determinations of the concentration of an analyte of interest, or a determination of the optical properties of an object, with an improved signal-to-background level.

These and other objects and features will be apparent from the description and the accompanying drawings.

SUMMARY OF THE INVENTION

The present invention features an improved apparatus and methods for carrying out testing for concentration of constituents of interest or determining the optical properties of an object, preferably in a non-invasive manner. U.S. patent application Ser. No. 914,265 discloses an apparatus which uses, and expands upon, an analog of human vision to develop data through non-invasive testing which is much improved from that available through classic spectrophotometric measurements. In its various embodiments, the present invention discloses improvements on the basic concept and apparatus described in the aforementioned U.S. patent application Ser. No. 914,265; in particular, the present invention concerning ways of improving the signal-to-background (or noise) ratio such that the data stream is improved. As such, these improvements are important as they allow better standardization and use of the basic invention in circumstances where the more simplified apparatus might not provide meaningful data.

The basic apparatus such has been described in the aforementioned patent application, which is useful for non-invasive testing of the concentration of a constituent or analyte of interest, e.g., in a mammalian blood stream, has (1) a light source generating illuminating radiation, preferably infrared radiation, for illuminating a portion of mammalian tissue, (2) a sample chamber for fixing the portion of the mammalian tissue in a substantially fixed location relative to the light source, (3) detection means having a plurality, that is, at least 2, preferably at least 3 or 4, detectors, each of the detectors having a separate peak spectral response and an overlap in overall spectral response with at least one other detector. While the detector itself can provide the aforementioned spectral response, preferably the detector has in concert a filter which transmits a portion of the spectrum of illuminating radiation emitted by the light source. Each of these filters has a separate peak transmission response and broad enough transmission response such that there is partial overlap in transmission characteristics with at least one other of the filters. The apparatus also includes analysis means for analyzing the outputs from the detectors to generate a signal indicative of the concentration of the constituent or analyte or the optical properties of an object.

In one aspect of the invention, the improvement is in the form of arranging (and manufacturing) the apparatus such that "congruent sampling" is achieved. In congruent sampling, each detector receives the radiation from substantially the same portion of the sample transmitted (or reflected or emitted) in the same direction so that all the rays emerging in all directions from each point of the sample are incident in the same direction on each detector. With congruent sampling, the detectors are superimposable; that is, if a transformation (or translocation) was made from the position of one detector to the position of another detector the identical optical sampling is achieved. Congruent sampling guarantees that the optical beam path from the sample to each detector is both of equal length and of equal angles, thereby eliminating a substantial portion of error caused by viewing from unequal distances or angles. This aspect of the invention is particularly relevant in dealing with inhomogeneous samples, since it minimizes errors due to the inhomogeneity. Further, the use of congruent sampling allows a larger source and a larger illumination area, thus allowing the delivery of the same cumulative power to the detector without using a very small spot. For measurements of a body part, this minimizes discomfort and allows greater source selection flexibility. Congruent sampling, as well as some of the other improvements described herein, also assist in correcting for modifications in response due to temperature or changes in refractive index. These effects may arise in the instrument or the sample itself.

Preferably, in this and all of the other aspects of the invention, infrared radiation in the 700–2500 nm range is used as the illuminating radiation, although wavelengths as low as 500 nm or up to about 10,000 nm may provide meaningful information and are not ruled out. If three detectors are used, the analysis means generates an output which is (or can be) an infrared analog of a location in a colorimetric three dimensional space; if more detectors are used, an output is generated which is an analog of an n-dimensional colorimetric space, where n is equal to, or less than, the number of detectors. One of the detectors that is often used in addition to the plurality of detectors is a black/white luminosity detector which is responsive to and overlaps the spectral response of all of the other detectors. This black/white luminosity detector is used to show the presence and absence of signals as a whole without regard to the specific wavelength. The analysis means can be a computer but preferably is a neural network which mimics the human mind. Neural networks are becoming more sophisticated and the use of this type of network provides a "learning curve" to the system as a whole. If the system is used for concentration testing, a sample chamber is normally required. The sample chamber can hold a mammalian body part such as fingers, ears, hands, foot, toe, wrist, tongue or even the forehead in fixed relation to the detectors. Basically, all that is needed for a non-invasive test measurement using this system is sufficient vascular tissue such that the blood vessel bed can be sampled to sufficient depth in either transmittance or reflectance mode so as to provide meaningful data.

The apparatus (and methods) are particularly useful in detecting the concentration of a broad family of analytes and constituents found in mammalian blood streams. Obvious choices for applicability of the invention include glucose, glucose indicating constituents (it may be possible to read a constituent that gives an indication of glucose level instead of glucose itself), cholesterol, lipids, hemoglobin and its variants, drugs of abuse and/or drugs of abuse indicating constituents. These drugs of abuse include not just narcotics and hallucinogens but also materials such as alcohol. Any analyte with absorption bands in the response range of the detectors can be used. Further, the apparatus can be used to measure water bands as well as the constituent of interest, thereby facilitating the determination of concentration. The constituent may shift the water bands toward its color which can provide the indicating activity even if the bands of the constituent itself are indistinct; that is, the fractional shift of the water bands may present the sought for information.

In another aspect, the invention features having at least two detection means or sets of detectors, each of said detection means either viewing a different portion of the sample, e.g., mammalian body or having a different set of filters from the other. Using either of these apparatus variations, one obtains two distinct sets of signals which can be correlated to concentration or the optical properties of the object. By correlating these two signal sets, one can obtain better signal-to-background values, since the alignment (or correlation) of the signals does not necessarily provide alignment of background, thereby smoothing the background and providing better-signal-to-background ratios. A preferred method of achieving this is to have different detection means for each of two fingers, possibly with different sets of filters for each, thereby getting two different sets of data that, however, are correlated to the same analyte concentration. If a single sample is used, the detectors, or most preferably the filters for each of the detection means, should have differing spectral transmission responses. The analysis means obtains an output from a first detection means which is an analog of a location in a colorimetric n-dimensional space, it obtains an output from the second detection means which is an analog of a location in an m-dimensional space, and compares the two outputs to provide a measure of the constituent of interest. Both m and n are equal to or less than the number of detectors in the respective detection means. If two distinct body parts are used, either with or without different filter sets on the separate detection means, there should be at least two sample chambers. Each of said sample chambers must be arranged such that the radiation passing through falls on only one, but not both, of the first and second detection means.

In still another aspect of the invention, at least one of the filters for the detectors in the detection means can be replaced by a filter which either has a spectral structure, such as a comb filter, or by a narrow pass filter, which has all of its transmission range overlapped by one of the other filters. A filter having spectral structure such as a comb filter is equivalent to a series of filters, yielding an approximation of more detectors. A sinusoidal filter is a preferred type of comb filter but a sine squared or other filter having spectral structure could be used. The advantage of using this type of filtering unit is that absorption bands for unwanted analytes can be eliminated even if they are in the active area by paralleling the absorption characteristics of the comb filter with those absorption bands, or selecting narrow band filters such that the absorption characteristics of the analytes do not overlap with the transmission characteristics of those filters.

In still a further aspect of the invention, an interrogation unit or means is included in the apparatus which interrogates the outputs from the detectors in a sufficiently rapid manner so as to allow differentiation of constituents of interest in arterial blood, as opposed to venous or tissue blood. This interrogation means can be the combination of the detection means and the analysis means so long as the electronics provides processing or collection of data which is sufficiently rapid so that the time of the arterial pulse is long compared with the interrogation time. Since the amount of blood in both the veins and tissues is substantially constant, this allows an approximation of the transmission or reflection from tissues and veins as a constant, thereby assisting in differentiating the arterial signal from background. The analysis means can use absolute values for transmission or reflection, or preferably, one can calculate a rate based on the slope of the arterial pulse signals.

In addition to the multiple variations on the apparatus, there also are corresponding method variations which form various aspects of the invention. For example, the congruent sampling or equal optical beam path/equal angle apparatus forms a method of minimizing the effect of sample inhomogeniety not only with respect to variability over the observed sample surface but also variability in sample transmission as a function of angle. This ensures that each detector in each detection means (or channel) sees only the same view of the same portion of the sample and that the detectors therefore process only color differences since the geometric and inhomogeniety effects are identical in all channels. The other methods provide similar advantages. Preferably, some combination of the apparatus described previously can be used; for example, two different body parts may be used with separate detector units and the processing should be sufficiently fast that an arterial pulse is seen by each of the detection filter units. This again minimizes the background level. An FTIR instrument could also be used to practice the methods of the invention if its orthogonal Fourier filters are replaced by a filter set such as is previously described and directing the outputs of these new filter functions to a unit which performs this described processing. Further, the invention can be practiced with a fluorescent object or sample if the filters or detectors are selected for the fluorescent radiation emitted by the sample rather than the illuminating radiation.

Other aspects and features of the invention will be more readily apparent from the following description and the drawing.

BRIEF DESCRIPTION OF THE DRAWING

FIGS. 3a–b show computer models of water and sugar peaks plotted as absorbance versus wavelength.

DETAILED DESCRIPTION OF THE INVENTION

The present invention provides improved non-invasive procedures for measuring the concentration of a constituent of interest that has absorbance, emittance, or reflectance bands in a selected region of the electromagnetic spectrum, preferably 500–10,000 nm, most preferably 700–2500 nm. This invention can be used to determine optical properties of a sample or object in addition to making concentration measurements. The apparatus and methods are improvements to the basic concept described in U.S. patent application Ser. No. 914,265. The apparatus and methods of the prior application are based, in part, on the recognition that present problems associated with non-invasive concentration measurements that use radiation as a probe relate to the type of information that is obtained, e.g., from spectrophotometers, rather than the processing of the information itself.

Although using different analysis techniques can clarify what information has been obtained, these analysis techniques cannot generate results better than the underlying information obtained. By applying an analog of color perception to concentration measurements, particularly forming a near infrared parallel of the three different pigments of the cones of the retina, significantly better information relating to concentration can be obtained. Since in color perception "color constancy" is maintained under extreme variations in illumination, the use of neural networks or digital computation to process information in a manner more similar to the information processing of the eye-brain is preferred. Color constancy is the capacity to successfully recover the reflected, emitted, or transmitted color of an object regardless of the composition or intensity of the ambient illuminating radiation. A further description of color constancy is found in Dufort and Lumsden, "Color categorization and color constancy in a neural network model of V4", *Biol. Cybern.* 65, 293–303(1991), the disclosure of which is incorporated herein by reference.

The improvements herein to the basic invention set forth in U.S. patent application Ser. No. 914,265 concern improved means of obtaining data such that the signal desired is maximized and the background signal (or noise) is minimized. Each of the embodiments described herein provide alternate means to achieve this same advantage. In fact, a preferred apparatus could have a combination of several of these embodiments used in concert.

Figure 1A:
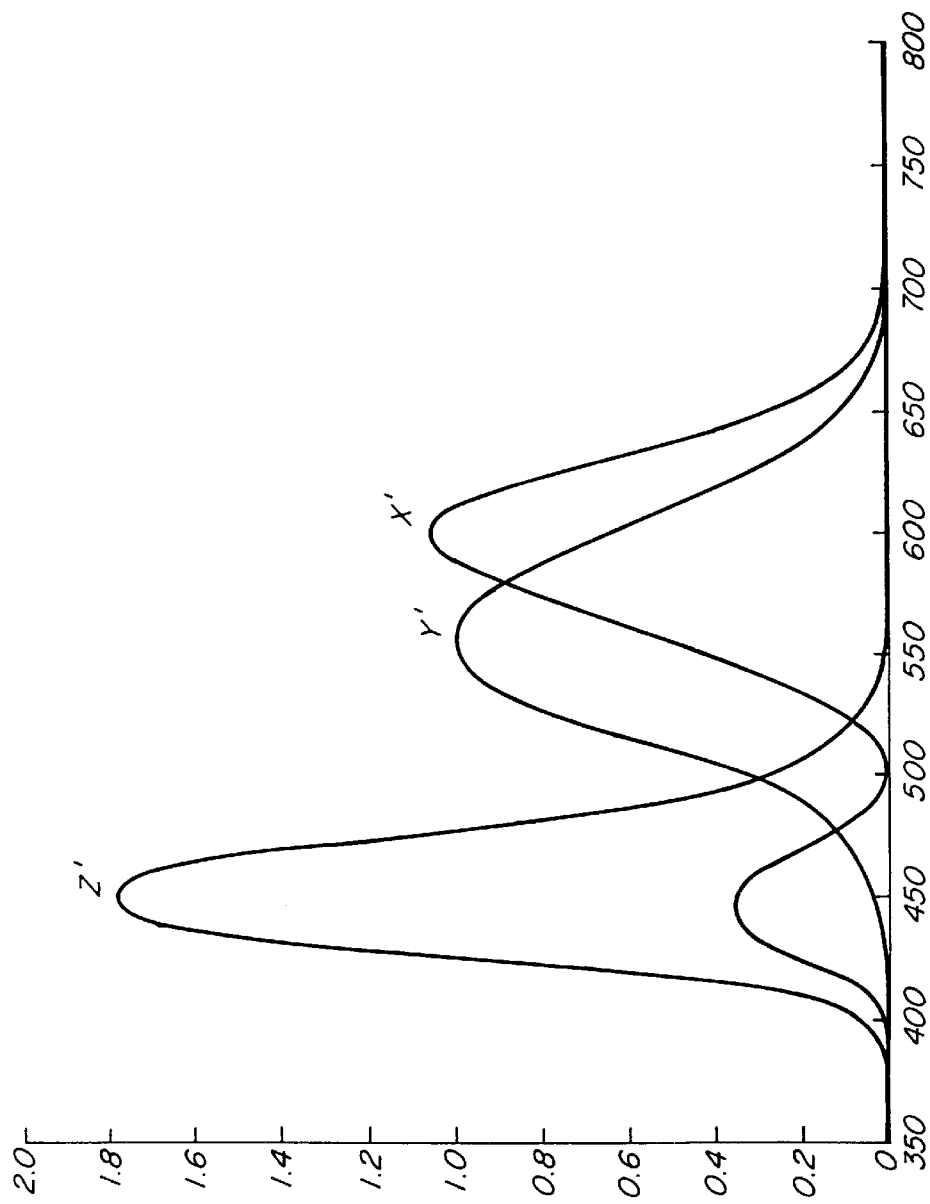
FIGS. 1(a), (b) show the CIE 1931 chromaticity plot, shown in standard spectral tristimulus values (FIG. 1a) and normalized form (FIG. 1b)
Figure 1B:
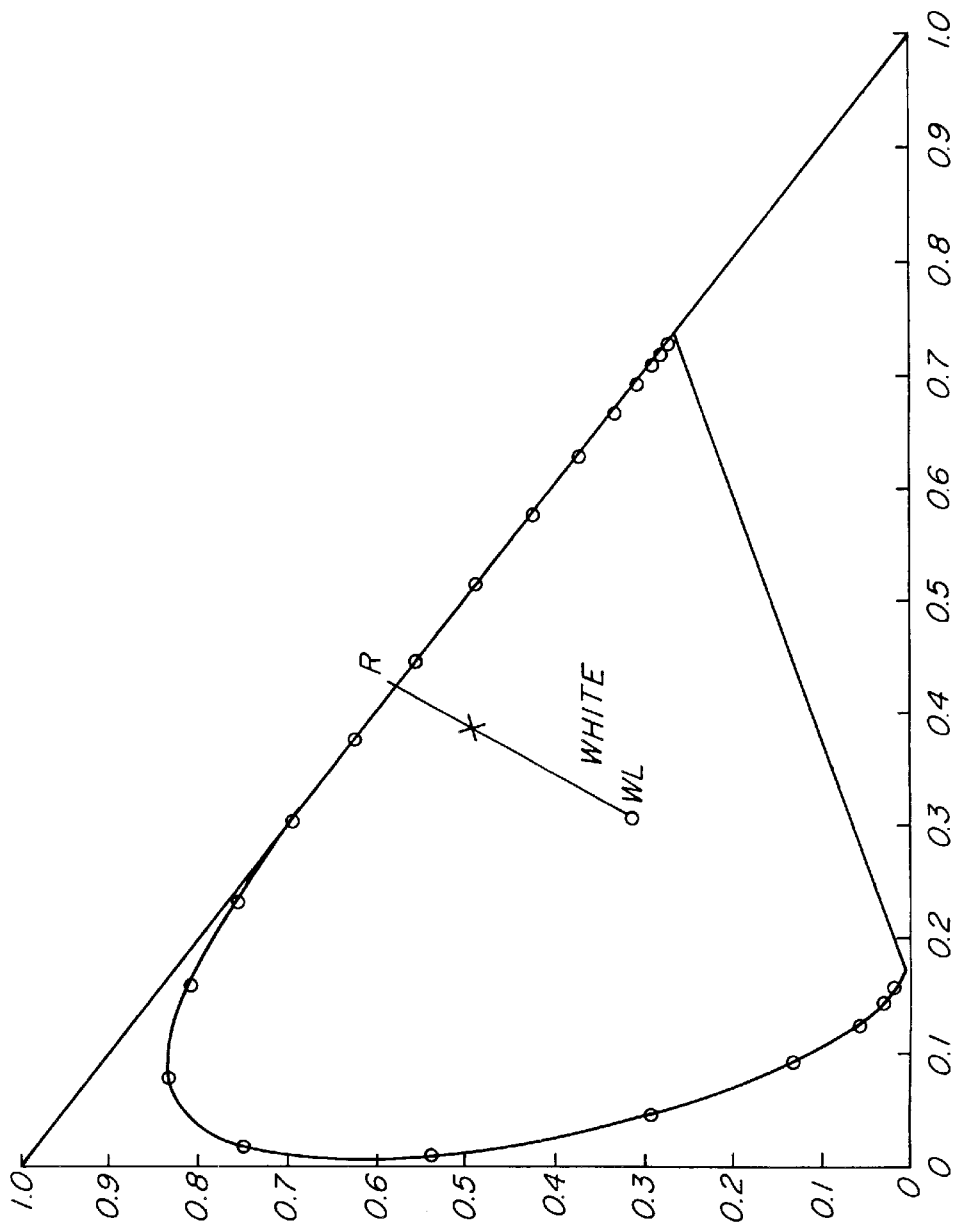
Figure 2:
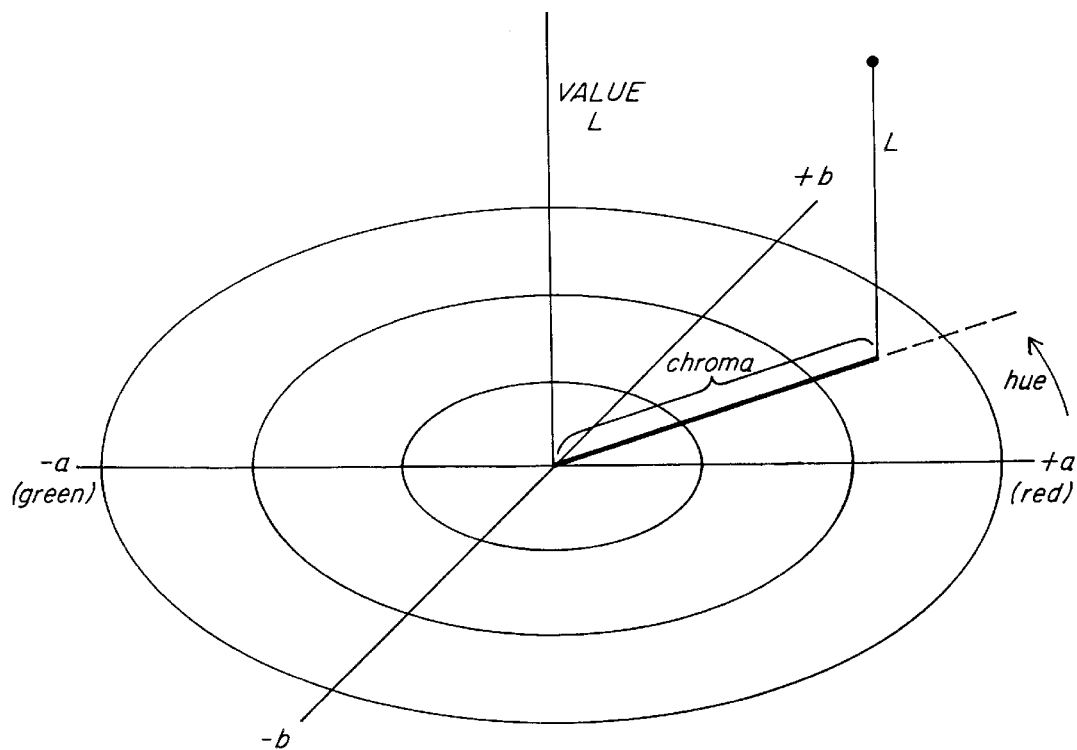
FIG. 2 is a three dimensional plot of color in terms of hue, chroma and value.

FIGS. 1 and 2 show different ways of handling data in classic instrumental colorimetry. FIG. 1a shows the CIE 1931 standard color matching functions, which approximate the spectral response of the three types of cones in the human retina. FIG. 1b, a so-called chromaticity plot, is a convenient two dimensional representation of the systematic variation of this standard observer to monochromatic light of different wavelengths. Each point on the continuous curve in FIG. 1b is plotted as a normalized (X, Y) pair, where the values are obtained from the three response curves in FIG. 1a by dividing by the sum of all three response, according to the formulas:

$$D=x'+y'+z'$$

$$X=x'/D$$

$$Y=y'/D$$

$$Z=z'/D$$

This normalization lead to the result X+Y+Z=1 and completely defines the relative values of X, Y, and Z. Accordingly, specification of X and Y on the two dimensional plot in FIG. 1b is sufficient to specify Z as well. Monochromatic light passes at the indicated points along the horseshoe shaped curve in FIG. 1b and with this normalization, pure monochromatic light falls at the same point along the curve irrespective of its intensity or brightness so the intensity (nominally D) must be specified separately. White light (of any intensity) falls at the point X=0.307 Y=0.314 (the point designated WL on FIG. 1b).

The light received from real objects, which is not monochromatic, fall at points within the interior of the curve. The hue or dominant "color" of such real objects is defined as the perceived color of the monochromatic light which lies at the intersection of the outer horseshoe-shaped curve with a line from the white light point (WL) through the object's location on the plot. Line WL-R is an example of this type of line and point R shows the "hue". The saturation, or chroma, of the light is a measure of how far along the line from "white" to "pure" color the object's location is found.

The hue-chroma coordinate system in FIG. 1b is irregular, however, in that the length of the vector from the center to the outer curve changes significantly with wavelength. FIG. 2 is an alternative, cylindrical coordinate system in which the hue is defined by the angular rotation from an arbitrarily chosen green-red axis, and the chroma is defined as the radial distance from the center. Here the density, or value of the light is explicitly included as the third cylindrical coordinate. The AB plane in FIG. 2 is equivalent to the XY plane in FIG. 1b.

In classic instrumental colorimetry, only the color was sought, so that the relative direction of the vector in the three dimensional space was what was important, not the amplitude. When used for color comparison, the tristimulus system outlined in conjunction with FIG. 1 reduces the dimensionality of the vector space from three to two through the use of normalization. It should be noted, however, that this self-normalized approach introduces a degree of linearization for incremental color changes which alter the three components of the xyz vector by relatively small amounts, particularly when the changes are nearly perpendicular to the starting vector itself.

These instrumental tristimulus systems do not, however, perform color vision, but rather are intended to characterize colors so they can be duplicated reliably. In particular, these systems are quite sensitive to changes in the illuminant spectrum and, hence, are not duplicating the color constancy features of mammalian color vision.

The present invention sets up an analog of visual color perception using N detectors which can form a partially degenerate N-dimensional vector space. The dimensionality is preferably reduced by at least one because the vector is normalized, and perhaps by more than one because the detector curves overlap strongly so that the resultant detector signals are partially correlated. Many different normalizations, such as the sum of one or more of the N signals or the length of the vector, may be used. The resultant vector space is used to characterize a higher dimensional analog of hue and chroma to quantify the amount of the "color" of glucose in the observed specimen.

FIG. 3 is a series of computer-generated simulations of the absorbance spectrum of water and sugar in the 700–1200 nm range. The locations, magnitudes, and widths of the peaks shown are taken from a variety of sources in the literature. The three indicated peaks near 1000, 920, and 840 nm appear together, for example, in the work of Koashi et al. described in U.S. Pat. No. 4,883,953, superimposed on a broad background offset. Interpretation of such reported results requires care to separate glucose spectral features from instrumental artifacts. The difficulty in obtaining reliable glucose spectra is well-known, and follows from the small magnitude of the absorption by glucose in this spectral range and from the fact that the water content and refractive index of solutions change when glucose is added. The instrumentally observed changes in detector signals in this spectral range are a mixture of increased absorbance from glucose, decreased absorbance due to the displaced water and changes in instrumental throughput due to refractive index and temperature variations during the experiments. The final result for the glucose spectrum itself is highly dependent on the accuracy of the corrections for these effects. Nevertheless, the general features shown in FIG. 3 emerge as suitably descriptive to guide the selection of detector response functions to implement the present invention.

The peak (WOH) shown in FIG. 3a at 960 nm is attributed to absorption by the OH group in water. The glucose peak (GOH) near 1000 nm in FIG. 3b is also attributed to OH absorption, with its location shifted to higher wavelength as a result of local field distortions at the OH sites on the glucose due to the other atoms on the molecule. The size of the glucose peak can be readily estimated on the assumption that there is no loss of total absorbance, but only a shift. Thus, pure water is roughly 56 molar; glucose at 1 gram/dl (=10 grams/liter) and a molecular weight of 180 is roughly 10/180=0.056 molar, 1000 times smaller than pure water. Each molecule of glucose, however, carries 5 OH groups: hence the glucose is roughly 0.28 molar in OH groups, and should have an absorbance about 200 times smaller than pure water. Scaling from FIG. 3a, the expected magnitude of the shifted OH peak from glucose is thus of the order of 0.001 absorbance units.

The peaks shown in FIG. 3b near 920 nm (CCH) is attributed to the stretch mode of the CH bonds in glucose. Its magnitude relative to the shifted OH peak (GOH) in FIG. 3b is taken coarsely from the data presented by Koashi, as is the smaller peak at 840 nm. These three peaks are consistent with the spectral correlation plots presented by Rosenthal in U.S. Pat. No. 5,028,787, which also indicate the possible presence of another slight peak in the 750 nm range, which has not been included in FIG. 3b.

FIG. 3b also includes an estimate of the relative size of the absorbance of the water displaced by glucose at 1 gram/dl concentration. This was obtained from FIG. 3a using the tabulated specific gravity of 1.0039 (ref. Handbook of Chemistry and Physics) for such a glucose solution. Thus, if 1 gram of glucose is added to 99 grams of water, the result is 100 grams of solution filling 100/1.0039=99.61 ml. A full deciliter of this solution then contains 99.39 grams of water (and 1.0039 grams of glucose). By comparison a full deciliter of pure water would contain 100 grams of water. Thus the change to approximately 1 gram/dl concentration of glucose reduces the water content of the solution by 0.61 grams; the magnitude of the absorbance of this displaced water is about 100/0.61 or about 164 times smaller than that of pure water.

Figure 3C:
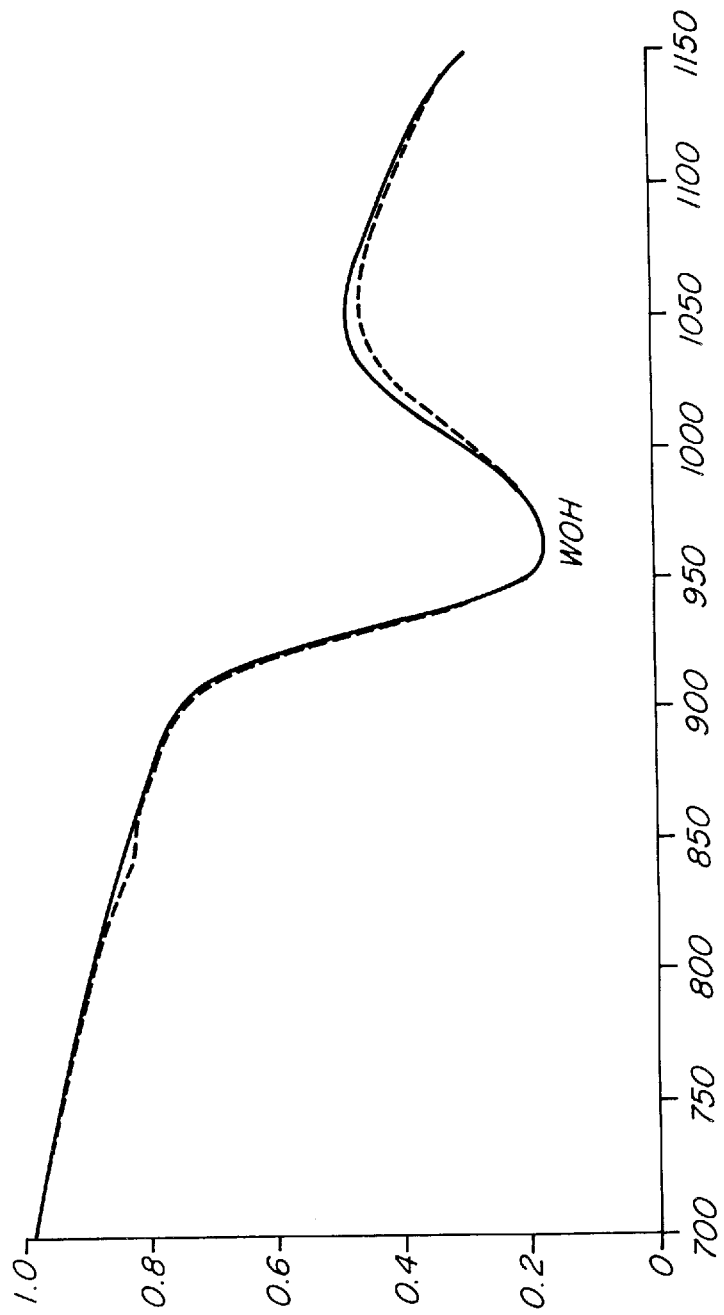
FIG. 3c shows the composite transmission spectrum of a glucose solution.

FIG. 3c shows the calculated impact of these broad and shall glucose features on the transmission spectrum of four centimeters of water. Note that the glucose concentration has been increased to 10 grams/dl to render the difference between the curves visible. The major impact of the glucose absorbance is to change the apparent shape of the 960 nm water band (WOH). The total change is slight: at the clinically significant range of 0.05–0.5 grams/dl, the changes would fall within the width of the line on the full scale plot in FIG. 3c.

The need to detect and quantify such small changes in the presence of other changes in the band shape due to temperature effects and the impact of other constituents of the fluid which may also alter the shape place a premium on making optimal use of the entire signal change due to glucose, i.e., by integrating the full change with different weights on a plurality of overlapping detectors. The information in FIG. 3 may make it possible to "tune" the filters to emphasize the CH stretch and shifted OH band contribution, and diminish that from the unshifted OH band contribution, in one or more detectors, while doing the reverse in other detectors.

Figure 4A:
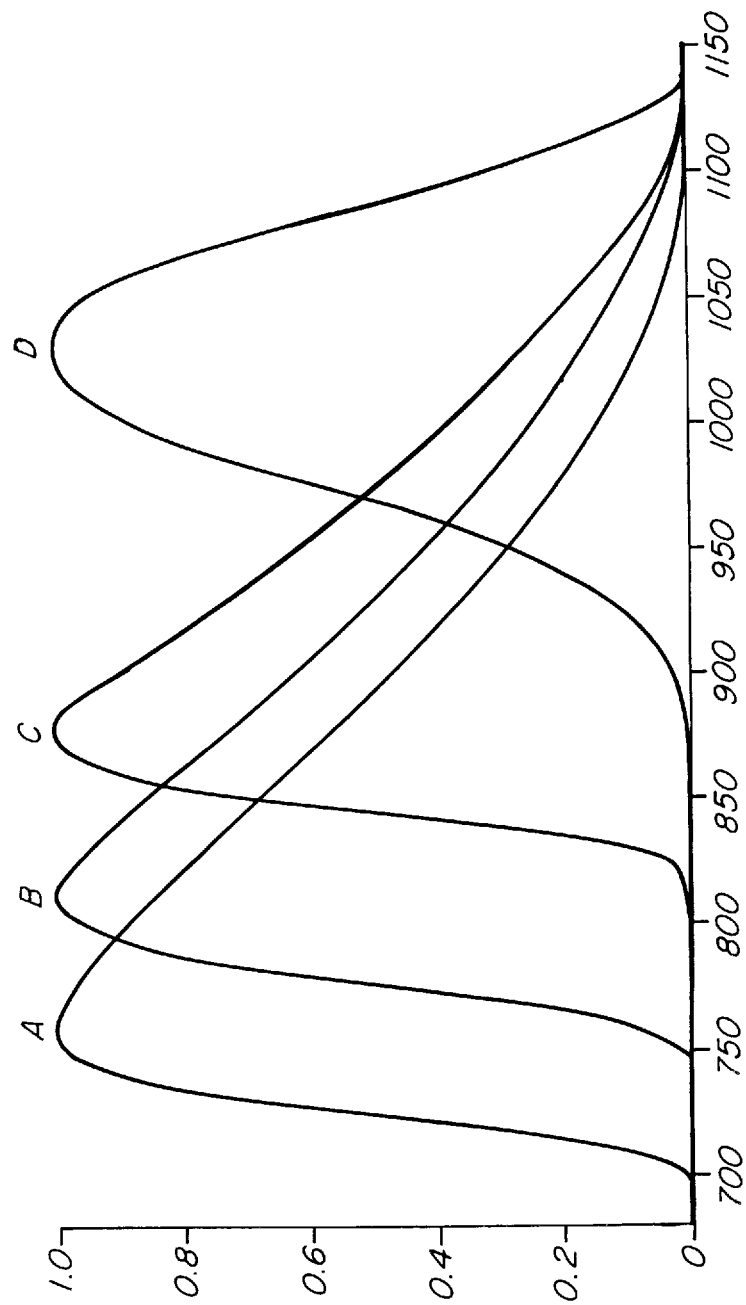
FIGS. 4a and 4b are plots of relative spectral response versus wavelength for two different filter sets, one having four different filters and the other with six different filters.

FIG. 4a shows one set of filters which could be used with the invention. Each of the four response curves is a composite of the spectral response of the silicon detector (HAMMATSU S2387 Series) and the transmission of at least one 3 mm thick Schott glass filter. If a pair of filters is used (as in filter sets A, B and C), the filters are in series. In each of case A, B and C, the first illuminated filter in the pair is a long-pass filter whose transmission rises with increasing wavelength (RG9, RG780, RG850, respectively). The second filter, made of KG2 glass, acts as a short-pass filter whose transmission falls with increasing wavelength. For the D detector, a single filter such as a RG1000 filter is used and the decrease in response at the highest wavelengths is produced by the spectral response of the silicon detector itself.

As can be seen from this figure, each of the filters has a separate peak transmittance range, and overlaps with the response of the others. In particular, the A, C, and D filters comprise a trio which implements an approximate translation of the cone response curves from the visible into the near infrared, as described in U.S. patent application Ser. No. 914,265.

Figure 4B:
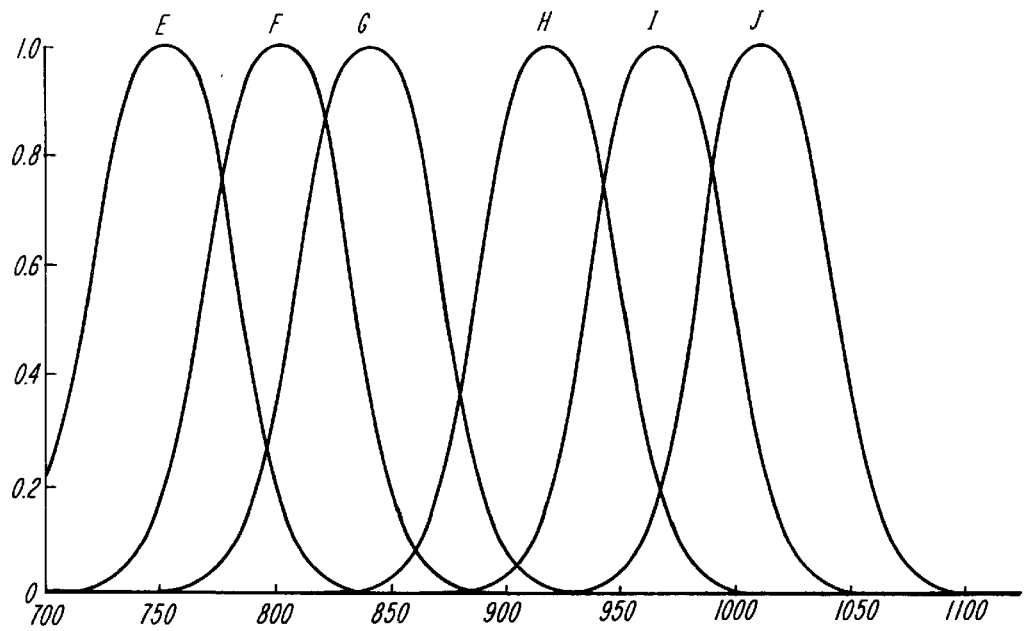

However, the filter set in FIG. 4a is not an efficient match to the spectra of glucose and water, because a large portion of the response is concentrated in the short wavelength region where these constituents are least absorbing. FIG. 4b shows an alternative set of filters which could increase the percentage impact of the various bands in FIG. 3 on the total signal in each detector. This shows overlapping broad-band interference filters which are commercially available from the Corion Corporation (their P70 series) to bracket the 960 nm water peak so as to enhance the size and uniqueness of the signal changes which result from changing glucose concentration.

Figure 9:
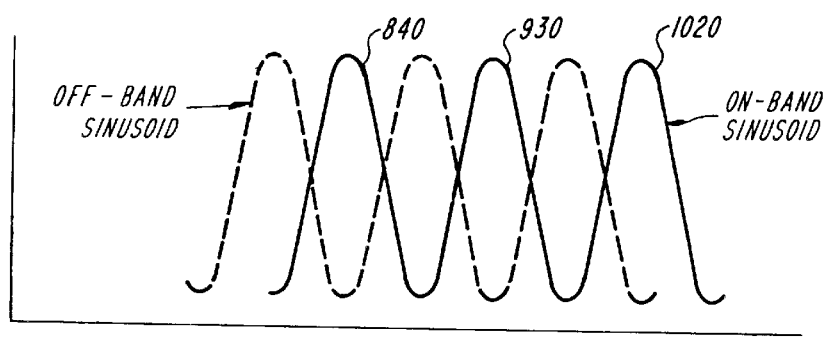
FIG. 9 shows the transmittance of a "comb" filter useful in another embodiment of the invention.
Figure 10A:
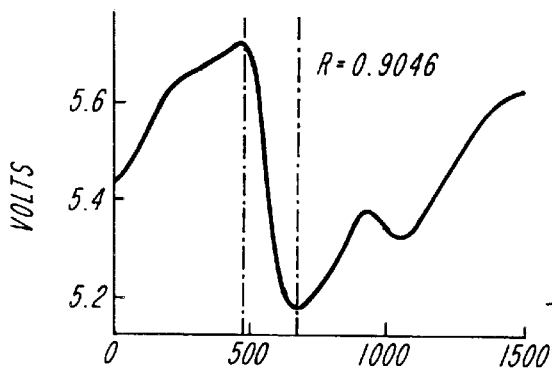
FIGS. 10(a–b) shows pulse data taken from an instrument using the principles of another embodiment of the invention.
Figure 10B:
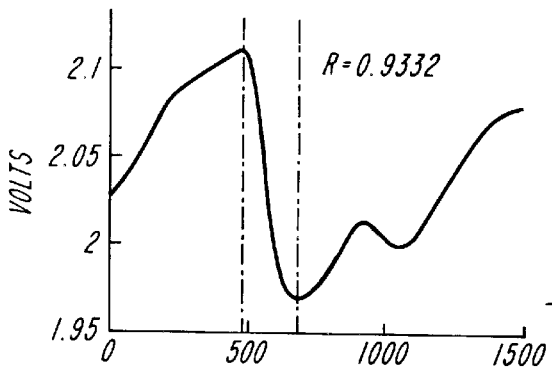
Figure 10C:
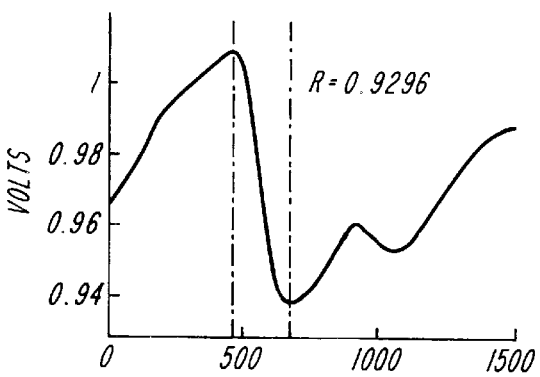
Figure 10D:
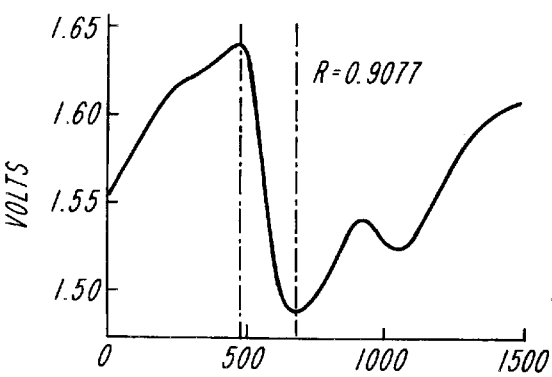
Figure 11A:
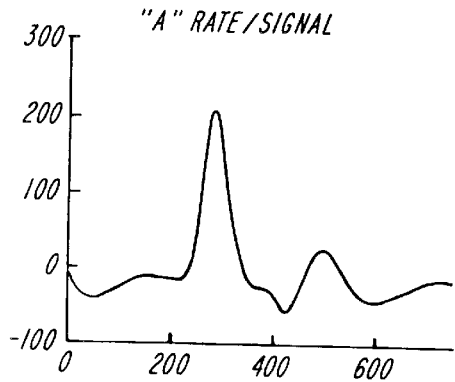
FIG. 11 is rate data using the same data and apparatus as is used in FIG. 10.
Figure 11B:
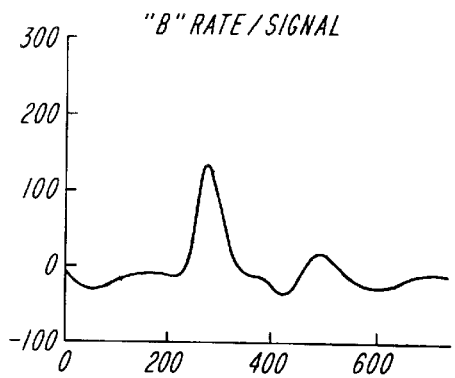
Figure 11C:
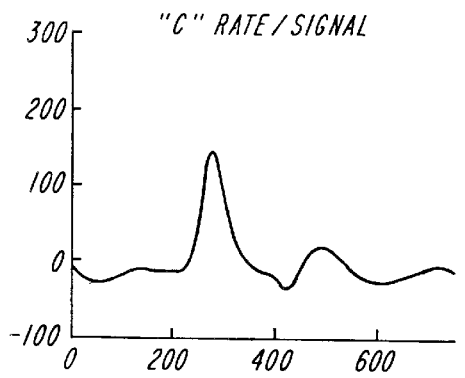
Figure 11D:
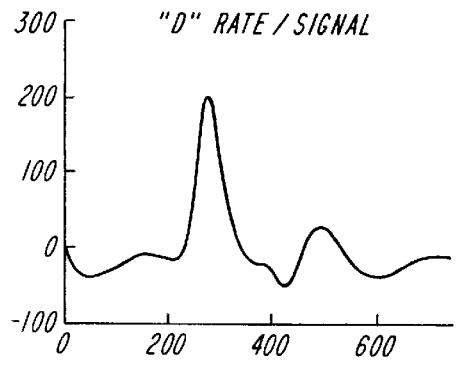

It is also possible to create filters with multiple passbands so that, for example, the H and J filters in FIG. 4b could be combined into a single composite passband. Similarly, a comb or sinusoidal filter, as shown in FIG. 9, could be used to integrate the signal from all three of the glucose peaks in FIG. 3, with a similar but spectrally displaced filter being used to de-emphasize the spectral regions which contain the glucose features. The width, shape, and amplitude of each lobe of the comb, and the number of lobes in each set, can be adjusted to optimize the separation of signal and background. To achieve the desired self-consistent normalization of the signals, each detector signal could be divided, for example, (i) by the vector length calculated from all of the signals together, (ii) by the simple sum of all of the signals, (iii) by the signal observed through a single broadband filter which overlapped most of the spectral range covered by the full set, or even (iv) by the signal observed in a narrow band filter placed at an appropriate location within the range. Such normalization techniques and related ones are well known in the art of data processing, and are not restricted to the one delineated above; the important quality is that the filter response curves overlap, and be matched in width and location to the broad and shallow spectral features of the analyte of interest.

Figure 6:
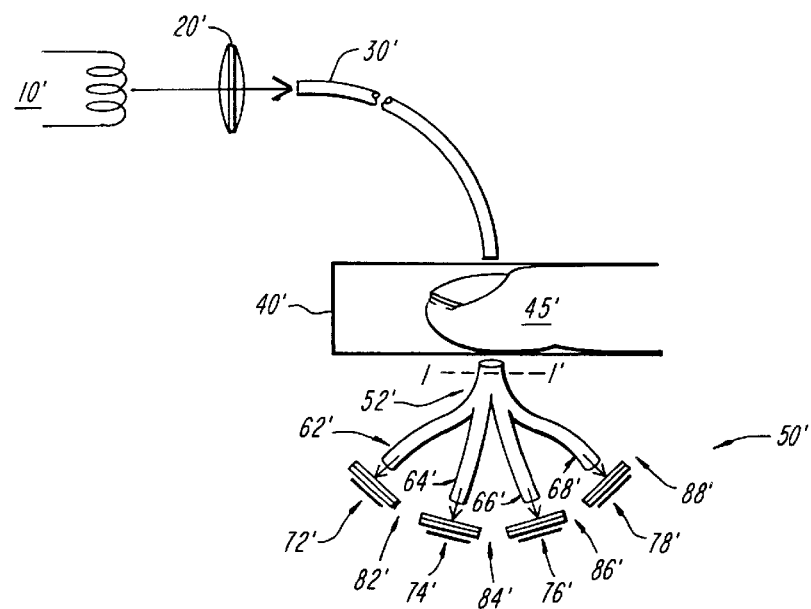
FIG. 6 is a schematic illustration of the device using a fiber optic bundle to provide equal distance and equal angle to the detectors.
Figure 5A:
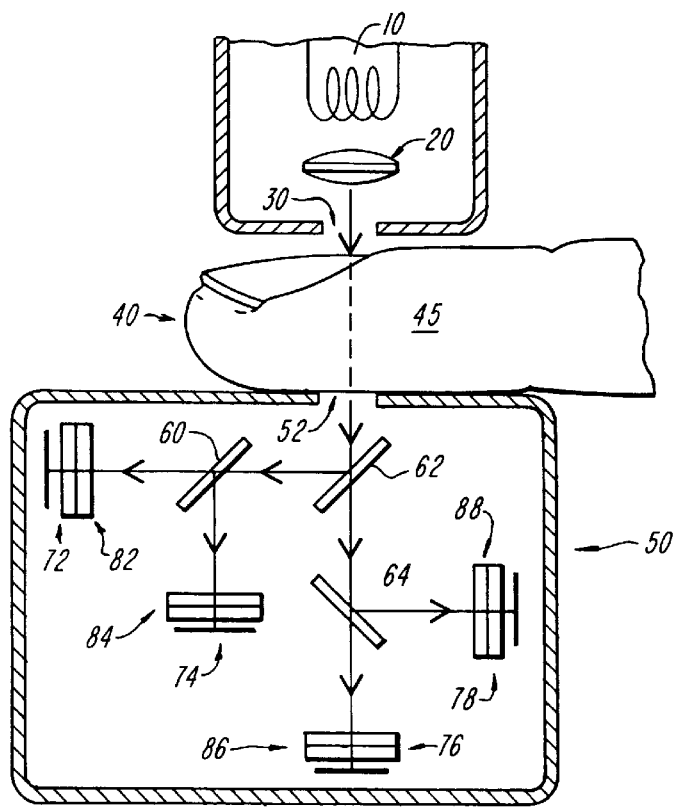
FIGS. 5a and b are two parallel embodiments of the invention showing a method of providing detectors which all view the same portion of the sample at the same optical beam path through the same solid angle, with FIG. 5b having a sufficient number of detectors to parallel the two detector means embodiment of FIG. 8.

FIGS. 5 and 6 both show attempts to cure one of the problems associated with any type of radiation measurement, the inhomogeneity derived from physical differences in the view of the detectors relative to the sample. With any physical object, particularly something as inhomogenious as mammalian body part, if the optical beam paths from the sample to the detector, and the solid angles over which they operate, are not equal, the device itself may cause an unwanted error (or at least a reduced signal-to-background response). The basic concept of the devices illustrated by these Figures is that the detectors collect light leaving points at the entrance aperture congruently. "Congruent," as used herein, means that the light collection efficiency at each point in the extended object being viewed, relative to the other points in the object, is the same for each detector. In other words, the images for each detector should be fully superimposable, so that, they cover the exact same solid angle at the same distance. The device illustrated in FIG. 5 achieves this by using a series of beam splitters to make the optical beam path such that the detectors all receive the same signal at the same distance and same angle. The device of FIG. 5 has a lamp 10 which generates the illuminating radiation, preferably infrared radiation in the 700–2500 nm range. The light from this lamp 10 is focused by a launch lens 20 through an aperture 30. Aperture 30 leads to a sample chamber 40, which is shown having a portion of the finger 45 therein. Radiation transmitted through finger 45 goes through entrance aperture 52 in detection means 50. Because the size of transmitted signals is lower, reflectance measurements may be advantageous but reflectance can have other associated problems with stray radiation. Further, although a mammalian body part is preferred, any sample could be used. Detection means 50 has a series of beam splitters 60, 62 and 64 which split the light entering through entrance aperture 52 and send it to four detectors 72, 74, 76 and 78. Each of detectors 72, 74, 76 and 78 may have an associated filter 82, 84, 86 and 88, respectively. These detectors and their associated filters, which will be described in more detail below, all have different peak transmittance responses. Normally, they also have sufficiently broad transmittance response such that each detector has some overlapping spectrum of transmittance with at least one other detector.

The outputs from detectors 72, 74, 76 and 78 go to an analysis means, such as a computer or neural network (not shown), which provides data processing and generates a signal indicative of the concentration of the constituent of interest.

Figure 5B:
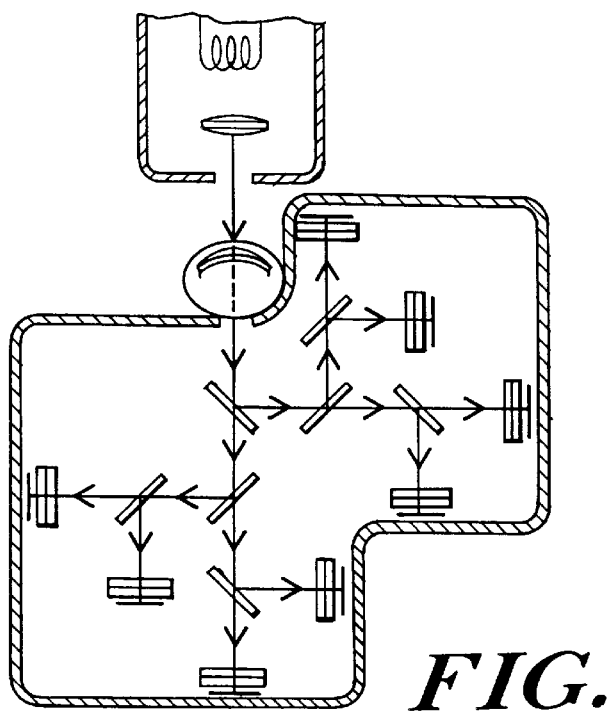

FIG. 5b shows a parallel device but with eight rather than four detectors and associated filters. This system could provide more accurate information by using more detectors and can be used in lieu of the two sample chamber/eight detector device shown in FIG. 8. For certain samples, segregating the data into two sets, each of four detectors, improved data can be obtained compared to a single detector set.

FIG. 6 illustrates another variation of the apparatus that provides substantially equal optical beam paths over the same solid angle. In this embodiment, lamp 10' and launch lens 20' can be identical to lamp 10 and 20 in embodiment of FIG. 5. In place of the entrance aperture to the sample chamber 30, a fiber optic cable 30' is used. Fiber optic cable 30' can either be a single fiber optic line or could be a fiber optic bundle such as is described later in conjunction with FIG. 7. Fiber optic cable 30' delivers the illuminating radiation, preferably infrared radiation in the 700–2500 nm range, to finger 45' is located. Although a finger is used in each of the Figures as a mammalian body part, other body parts including the forehead, toes, hands, feet, ears or wrist could be used, or a different type of sample could be used.

At the exit of sample chamber 40', the light transmitted through a fiber optic bundle 52' which takes the place of entrance aperture 52. The light is transmitted to detection means 50 through a fiber optic cable 52' which is bifurcated into four optic cables, 62', 64', 66' and 68'. The bifurcated fiber optic cable take the place of beam splitters 60, 62 and 64. Each of these fiber optic cables 62', 64', 66' and 68', lead to filters 82', 84', 86', and 88' which then transmit radiation to detectors 72', 74', 76' and 78'. The detectors and filters can be identical to those shown in FIG. 5.

Figure 7:
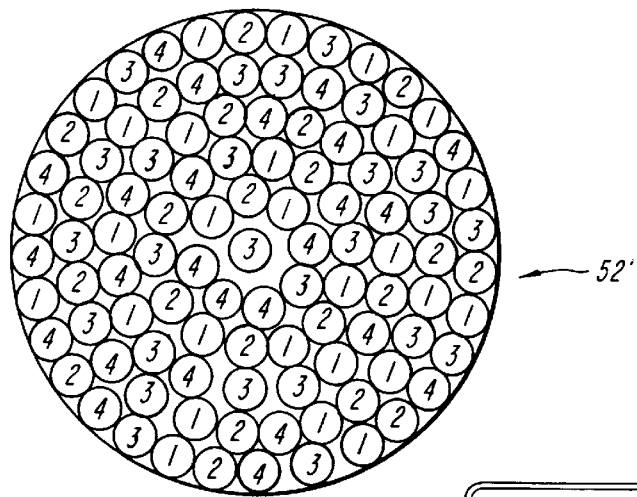
FIG. 7 is a detail of the fiber optic cable at a line 1—1 from FIG. 6.

The critical aspect of the device shown in FIG. 6 is the exit fiber optic cable bundle 52'. FIG. 7 shows a detail of this fiber optic cable bundle. FIG. 7 is a cross section of fiber optic bundle 52' through the line 1—1 prime on FIG. 6. As can be seen, this fiber optic bundle 52' contains many small fibers from the four output legs, 62', 64', 66', 68', intertwined so that they effectively sample each point at the input substantially equally. As shown in the Figure, all of the fibers having the number 1 go to bifurcated fiber optic cable 62', those having the number 2 go to fiber optic cable 64', those having the number 3 go to fiber optic cable 66', and those having the number 4 go to fiber optic cable 68'. While this is not exactly equivalent to the beam splitter arrangement FIG. 5 since the fibers do not exactly overlay each other, it is a very good first order of approximation if there are sufficient fibers, and the fibers are sufficiently small such that the mix of fibers about the cable is substantially random and equal.

Figure 8:
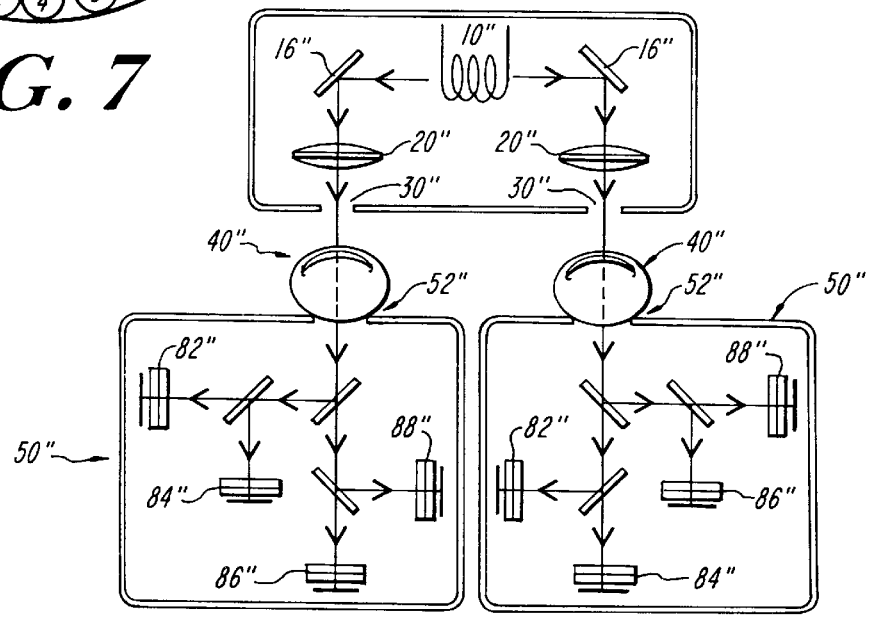
FIG. 8 shows an embodiment of the invention having two sample chambers and two detection means.

FIG. 8 illustrates another embodiment of the invention, one whereby two distinct n-dimensional spaces (or an n-dimensional space and an m-dimensional space) are generated and compared to yield an improved signal. In the embodiment shown, lamp 10" is used to provide the illuminating radiation which then goes to two mirrors 15" and 16" and onto a pair of launch lens 20". Each of entrance apertures 30", sample chambers 40", exit aperture 52" and detector means 50" are identical, both to that shown in FIG. 5 and to each other. However, in one sub-embodiment, the filters 82", 84", 86", and 88" in the two detection means 50" are different, yielding different n (or m) dimensional spaces. If these filters are different in that they have different peak transmittance, a different n (e.g., 3) dimensional space is generated. Each detector means generates a signal indicative of the concentration of the material of interest such as glucose and the two values can be compared by the analysis means to eliminate some of the contribution of background. One means of doing this is to generate a vector such as previously described, align the vectors, and add them which should give a higher vector amplitude in a single direction. Since the background components should not align, this yields better separation of signal and background. In the illustrated embodiment, two separate sample chambers 40" are shown. These sample chambers could be used for different body parts, such as two fingers, and a value generated even if the filter sets 82", 84", 86" and 88" are identical. Since the glucose values in the blood should be the same but the background values between the fingers are likely be different, this will promote differentiation of signal-from-background. In another aspect of this embodiment of the invention, a single sample chamber could be used but a beam splitter is placed near the exit aperture 52" from the sample chamber 40" such that the exiting transmitted radiation (or reflected radiation if that format is used) goes to two parallel detection means 50". By using different filter sets 82", 84", 86" and 88" on these two detection means 50" with the same input signal to the filters, two different n-dimensional (or an n-dimensional and m-dimensional) spaces are generated and the same advantages as previously described are obtained.

FIG. 9 shows the transmittance of a comb filter which could be used as one of the filters in a detection means in various aspects of the invention. This filter has a spectral structure such that it absorbs at certain wavelengths and transmits at other wavelengths. By aligning the absorbance bands of the filter with known bands of background constituents which are to be eliminated, e.g., water bands, one can obtain a more highly differentiated data stream. In place of the comb filter or other filter having a spectral structure, a single filter (or multiple filters) having a single, narrow transmittance peak which is overlapping with at least one of the other filters, could be used.

FIG. 10 shows actual arterial pulse data with an early form of the instrument described herein. The electronics of the instrument are such that one can collect data over a hundred times per second, much faster than the pulse rate. Accordingly, individual pulses can be shown on an absorbance versus time graph. In FIG. 10, each of subfigures 10A–10D show signal output voltages in volts versus time in milliseconds. Each of the four FIGS., 10A–10D, are made using the same type of photocells, silicon photocells, with different filter sets, specifically those with the response shown in FIG. 4a. Similarly, different photocells such as a mixture of silicon, lead sulfide and lead selenide cells could be used. The classic notch in the pulse wave form is seen in the figure. What is interesting is that the four different filters not only transmit different amounts of light (based on the transmittance of light of particular frequency), but also that the ratios of peak to trough voltages are different for each different detector. Using this type of information, a value of concentration can be obtained for the constituent of interest.

FIG. 11 uses the same data as FIG. 10 but plots it as a normalized rate rather than an absolute voltage value. The Y axis shows a percent change per second by plotting average slope across a unit time divided by the average value across a sliding sampling window in time, while the X axis gives time in milliseconds. The actual rate is inverted here but as is seen from FIGS. 11A–11D, the rate is different in each detector. Since these type of rate calculations have been used previously in pulse oximetry to provide information (albeit at limited wavelengths without overlap as the present case), a parallel can be made between the present invention and the rate calculations of pulse oximetry which are particularly useful. In fact, this type of arterial pulse processing can be used with any of the embodiments of the invention and it is particularly useful in conjunction with the dual sample chamber (e.g., two finger) method because the arterial components in each finger will correlate strongly. Similarly, it is believed that transmittance and reflectance changes from the arterial pulse will improve results using the present methods and apparatus. By using only the arterial pulse, much of the background can be eliminated and more meaningful data may be generated.

Those skilled in the art may appreciate the other advantages and uses of the subject matter disclosed herein. Such other advantages, uses and embodiments of the apparatus and methods described herein are included in the following claims.

What is claimed is:

1. In an apparatus for determining the optical properties of an object having:

a radiation source generating a spectrum of illuminating radiation for illuminating a portion of said object;

detection means having three or more detectors adapted to generate an output, each of said detectors having a spectral response in a portion of said spectrum of illuminating radiation emitted by said radiation source, each of said detectors having a separate peak spectral response and at least a partial overlap in spectral response characteristics with that of at least one other of said detectors; and analysis means for analyzing said outputs from the detectors to generate a signal indicative of the optical properties of said object;

the improvement comprising:

said apparatus being constructed such that each of said detectors is located such that it congruently samples the radiation from said object.

2. The apparatus of claim 1 wherein said illuminating radiation comprises infrared radiation in the 700–2500 nm range.

3. The apparatus of claim 1 wherein said analysis means generates an output which is an analog of a location in a colorimetric n-dimensional space, n being equal to, or less than, the number of detectors in said detection means.

4. The apparatus of claim 1 wherein said detector means further comprises a black/white luminosity detector which is responsive to and overlaps said spectral response of all of said three or more detectors.

5. The apparatus of claim 1 wherein each of said detectors comprises a filter which transmits or reflects a portion of said spectrum of illuminating radiation, each of said filters having a separate peak transmittance or absorbance response different from the peak transmittance or reflectance responses of the other filters of said detection means and at least a partial overlap in transmittance or reflectance response with at least one other of said filters.

6. The apparatus of claim 1 wherein said analysis means comprises a neural network.

7. The apparatus of claim 1 wherein at least one of said three or more detectors comprise a silicon photocell.

8. The apparatus of claim 1 comprising beam splitting means to allow said three or more detectors to be arranged to achieve congruent sampling.

9. The apparatus of claim 1 comprising a fiber optic cable bundle containing a plurality of optical fibers to allow said three or more detectors to be arranged to achieve congruent sampling.

10. In an apparatus for determining the optical properties of an object having:

a radiation source generating a spectrum of illuminating radiation for illuminating a portion of said sample;

detection means having three or more detectors adapted to generate an output, each of said detectors having a spectral response in a portion of said spectrum of illuminating radiation emitted by said radiation source, each of said detectors having a separate peak spectral response and at least a partial overlap in spectral response characteristics with that of at least one other of said detectors; and analysis means for analyzing the outputs from said detectors to generate a data signal component indicative of the optical properties of said object;

the improvement comprising:

having at least two detection means, a first detection means generating a first data stream formed of a composite of a data signal component indicative of said optical properties of said object and a background component, and a second detection means generating a second data stream formed of a composite of a data signal component indicative of said optical properties of said object and a background component; and said analysis means comprising means adapted for comparing said first data stream with said second data stream in order to generate an information signal indicative of the optical properties of said object while rendering the interfering features of the background from said first data stream and said second data stream to be less distinct than the background is in either data stream individually.

11. The apparatus of claim 10 wherein each of said detectors comprises a filter which transmits or reflects a portion of said spectrum of illuminating radiation, each of said filters having a peak transmittance or reflectance response different from the peak transmittance or reflectance responses of the other filters of said detection means and at least to a partial overlap in transmittance or absorbance response with at least one other filter, said first detection means having a first set of filters and said second detection means having a second set of filters, and said first and second sets of filters having differing transmittance or reflectance responses.

12. The apparatus of claim 10 wherein said illuminating radiation comprises infrared radiation in the 700–2500 nm range.

13. The apparatus of claim 10 wherein said analysis means generates an analog of a location in a colorimetric n-dimensional space from said first data stream, where n is equal to or less than, the number of detectors in each of said first detection means; an analog of a location in a colorimetric m-dimensional space from said second data stream, where m is equal to or less than, the number of detectors in said second detection means; and compares said locations to generate said data signal component indicative of the optical properties of said object.

14. The apparatus of claim 10 wherein at least one of said detection means further comprises a black/white luminosity detector which is responsive to and overlaps said spectral response of all of said three or more detectors in said detection means.

15. The apparatus of claim 10 wherein said analysis means comprises a neural network.

16. The apparatus of claim 10 wherein at least one of said three or more detectors comprises a silicon photocell.

17. In an apparatus for determining the optical properties of an object having:

a radiation source generating a spectrum of illuminating radiation for illuminating a portion of said object;

detection means having three or more detectors adapted to generate an output, each of said detectors having a spectral response to a portion of said spectrum of illuminating radiation emitted by said radiation source, each of said detector having a separate peak spectral response and at least a partial overlap in spectral response characteristics with that of a least one other of said detectors; and analysis means for analyzing the outputs from said detectors to generate a data signal component indicative of the optical properties of said object;

the improvement comprising:

having at least two detection means, a first detection means adapted to receive radiation transmitted or reflected from a first object portion, said first detection means generating a first data stream formed of a composite of a data signal component indicative of said optical properties of said object and a background component, and a second detection means adapted to receive radiation transmitted or reflected from a first object portion, said second detector means generating a second data stream formed of a composite of a data signal component indicative of said optical properties of said object and a background component; and said analysis means comprising means adapted for comparing said first data stream with said second data stream in order to generate an information signal indicative of the optical properties of said object while rendering the interfering features of the background from said first data stream and said second data stream to be less distinct than the background is in either data stream individually.

18. The apparatus of claim 17 wherein each of said detectors has a filter with a peak spectral response different from the peak spectral responses of the other filters of said detection means and at least a partial overlap in spectral response with at least one other filter, said first detection means having a first set of filters and said second detection means having a second set of filters, and said first and second sets of filters having differing spectral transmittance or reflectance responses.

19. The apparatus of claim 17 wherein said illuminating radiation comprises infrared radiation in the 700–2500 nm range.

20. The apparatus of claim 17 wherein said analysis means generates an analog of a location in a colorimetric n-dimensional space from said first data stream, where n is equal to or less than, the number of detectors in each of said first detection means; an analog of a location in a colorimetric m-dimensional space from said second data stream, where m is equal to or less than, the number of detectors in said second detection means; and compares said locations to generate said data signal component indicative of the optical properties of said object.

21. The apparatus of claim 17 wherein at least one of said detection means further comprises a black/white luminosity detector which is responsive to and overlaps said spectral response of all of said three or more detectors in said detection means.

22. The apparatus of claim 17 wherein said analysis means comprises a neural network.

23. The apparatus of claim 17 wherein at least one of said three or more detectors comprises a silicon photocell.

24. In an apparatus for determining the optical properties of an object having:

a radiation source generating a spectrum of illuminating radiation for illuminating a portion of said object;

detection means having three or more detectors adapted to generate an output, each of said detectors having a filter which transmits or reflects a portion of the spectrum of illuminating radiation emitted by said radiation source, each of said filters having a separate peak transmittance or reflection response and at least a partial overlap in transmittance or reflectance characteristics with at least one other of said filters; and analysis means for analyzing the outputs from the detectors to generate a signal indicative of the optical properties of said object;

the improvement comprising:

having at least one of said detectors in said detection means has a filter associated therewith which is selected from the group consisting of comb filters having spectral structure such that it has absorbance bands in the portion of the spectrum over which it transmits or reflects radiation, and filters which have only a single narrow transmittance or reflectance range.

25. The apparatus of claim 24 wherein said illuminating radiation comprises infrared radiation in the 700–2500 nm range.

26. The apparatus of claim 24 wherein said analysis means generates an output which is an analog of a location in a colorimetric n-dimensional space, n being equal to, or less than, the number of detectors in said detection means.

27. The apparatus of claim 24 wherein said detector means further comprises a black/white luminosity detector which is responsive to and overlaps said spectral response of all of said plurality of detectors.

28. The apparatus of claim 24 wherein said analysis means comprises a neural network.

29. The apparatus of claim 24 wherein at least one of said three or more detectors comprises a silicon photocell.

30. In an apparatus for determining the optical properties of a fluorescent object having:

a radiation source generating a spectrum of illuminating radiation for illuminating at least a portion of said object;

detection means having three or more detectors adapted to generate an output, each of said detectors having a spectral response in a portion of the spectrum of fluorescent radiation emitted by said object upon illumination, each of said detectors having a separate peak spectral response and at least a partial overlap in spectral response characteristics with that of at least one other of said detectors; and analysis means for analyzing said outputs from the detectors to generate a signal indicative of the optical properties of said object;

the improvement comprising:

said apparatus being constructed such that each of said detectors is located such that it congruently samples the radiation from said object.

31. The apparatus of claim 30 wherein said fluorescent radiation comprises infrared radiation in the 700–2500 nm range.

32. The apparatus of claim 30 wherein said analysis means generates an output which is an analog of a location in a colorimetric n-dimensional space, n being equal to, or less than, the number of detectors in said detection means.

33. The apparatus of claim 30 wherein said detector means further comprises a black/white luminosity detector which is responsive to and overlaps said spectral response of all of said three or more detectors.

34. The apparatus of claim 30 wherein each of said detectors comprises a filter which transmits or reflects a portion of said spectrum of fluorescent radiation, each of said filters having a separate peak transmittance or absorbance response different from the peak transmittance or reflectance responses of the other filters of said detection means and at least a partial overlap in transmittance or reflectance response with at least one other of said filters.

35. The apparatus of claim 30 wherein said analysis means comprises a neural network.

36. The apparatus of claim 30 wherein at least one of said three or more detectors comprise a silicon photocell.

37. The apparatus of claim 30 comprising beam splitting means to allow said three or more detectors to be arranged to achieve congruent sampling.

38. The apparatus of claim 30 comprising a fiber optic cable bundles containing a plurality of optical fibers to allow said three or more detectors to be arranged to achieve congruent sampling.

39. In an apparatus for determining the optical properties of a fluorescent object having:

a radiation source generating a spectrum of illuminating radiation for illuminating a portion of said sample;

detection means having three or more detectors adapted to generate an output, each of said detectors having a spectral response in a portion of the spectrum of fluorescent radiation emitted by said object upon illumination, each of said detectors having a separate peak spectral response and at least a partial overlap in spectral response characteristics with that of at least one other of said detectors; and analysis means for analyzing the outputs from said detectors to generate a data signal component indicative of the optical properties of said object;

the improvement comprising:

having at least two detection means, a first detection means generating a first data stream formed of a composite of a data signal component indicative of said optical properties of said object and a background component, and a second detection means generating a second data stream formed of a composite of a data signal component indicative of said optical properties of said object and a background component; and said analysis means comprising means adapted for comparing said first data stream with said second data stream in order to generate an information signal indicative of the optical properties of said object while rendering the interfering features of the background from said first data stream and said second data stream to be less distinct than the background is in either data stream individually.

40. The apparatus of claim 39 wherein each of said detectors comprises a filter which transmits or reflects a portion of said spectrum of fluorescent radiation, each of said filters having a peak transmittance or reflectance response different from the peak transmittance or reflectance responses of the other filters of said detection means and at least to a partial overlap in transmittance or absorbance response with at least one other filter, said first detection means having a first set of filters and said second detection means having a second set of filters, and said first and second sets of filters having differing transmittance or reflectance responses.

41. The apparatus of claim 39 wherein said fluorescent radiation comprises infrared radiation in the 700–2500 nm range.

42. The apparatus of claim 39 wherein said analysis means generates an analog of a location in a colorimetric n-dimensional space from said first data stream, where n is equal to or less than, the number of detectors in each of said first detection means; an analog of a location in a colorimetric m-dimensional space from said second data stream, where m is equal to or less than, the number of detectors in said second detection means; and compares said locations to generate said data signal component indicative of the optical properties of said object.

43. The apparatus of claim 39 wherein at least one of said detection means further comprises a black/white luminosity detector which is responsive to and overlaps said spectral response of all of said three or more detectors in said detection means.

44. The apparatus of claim 39 wherein said analysis means comprises a neural network.

45. The apparatus of claim 39 wherein at least one of said three or more detectors comprises a silicon photocell.

46. In an apparatus for determining the optical properties of a fluorescent object having:

a radiation source generating a spectrum of illuminating radiation for illuminating a portion of said object;

detection means having two or more detectors adapted to generate an output, each of said detectors having a spectral response to a portion of the spectrum of fluorescent radiation emitted by said object upon illumination, each of said detector having a separate peak spectral response and at least a partial overlap in spectral response characteristics with that of a least one other of said detectors; and analysis means for analyzing the outputs from said detectors to generate a data signal component indicative of the optical properties of said object;

the improvement comprising:

having at least two detection means, a first detection means adapted to receive radiation transmitted or reflected from a first object portion, said first detection means generating a first data stream formed of a composite of a data signal component indicative of said optical properties of said object and a background component, and a second detection means adapted to receive radiation transmitted or reflected from a first object portion, said second detector means generating a second data stream formed of a composite of a data signal component indicative of said optical properties of said object and a background component; and said analysis means comprising means adapted for comparing said first data stream with said second data stream in order to generate an information signal indicative of the optical properties of said object while rendering the interfering features of the background from said first data stream and said second data stream to be less distinct than the background is in either data stream individually.

47. The apparatus of claim 46 wherein each of said detectors has a filter with a peak spectral response different from the peak spectral responses of the other filters of said detection means and at least a partial overlap in spectral response with at least one other filter, said first detection means having a first set of filters and said second detection means having a second set of filters, and said first and second sets of filters having differing spectral transmittance or reflectance responses.

48. The apparatus of claim 46 wherein said fluorescent radiation comprises infrared radiation in the 700–2500 nm range.

49. The apparatus of claim 46 wherein said analysis means generates an analog of a location in a colorimetric n-dimensional space from said first data stream, where n is equal to or less than, the number of detectors in each of said first detection means; an analog of a location in a colorimetric m-dimensional space from said second data stream, where m is equal to or less than, the number of detectors in said second detection means; and compares said locations to generate said data signal component indicative of the optical properties of said object.

50. The apparatus of claim 46 wherein at least one of said detection means further comprises a black/white luminosity detector which is responsive to and overlaps said spectral response of all of said three or more detectors in said detection means.

51. The apparatus of claim 46 wherein said analysis means comprises a neural network.

52. The apparatus of claim 46 wherein at least one of said three or more detectors comprises a silicon photocell.

53. In an apparatus for determining the optical properties of a fluorescent object having:

a radiation source generating a spectrum of illuminating radiation for illuminating a portion of said object;

detection means having three or more detectors adapted to generate an output, each of said detectors having a filter which transmits or reflects a portion of the spectrum of fluorescent radiation emitted by said object, each of said filters having a separate peak transmittance or reflection response and at least a partial overlap in transmittance or reflectance characteristics with at least one other of said filters; and analysis means for analyzing the outputs from the detectors to generate a signal indicative of the optical properties of said object;

the improvement comprising:

having at least one of said detectors in said detection means has a filter associated therewith which is selected from the group consisting of comb filters having spectral structure such that it has absorbance bands in the portion of the spectrum over which it transmits or reflects radiation, and filters which have only a single narrow transmittance or reflectance range.

54. The apparatus of claim 53 wherein said fluorescent radiation comprises infrared radiation in the 700–2500 nm range.

55. The apparatus of claim 53 wherein said analysis means generates an output which is an analog of a location in a colorimetric n-dimensional space, n being equal to, or less than, the number of detectors in said detection means.

56. The apparatus of claim 53 wherein said detector means further comprises a black/white luminosity detector which is responsive to and overlaps said spectral response of all of said three or more detectors.

57. The apparatus of claim 53 wherein said analysis means comprises a neural network.

58. The apparatus of claim 53 wherein at least one of said three or more detectors comprises a silicon photocell.

* * * * *

UNITED STATES PATENT AND TRADEMARK OFFICE
CERTIFICATE OF CORRECTION

PATENT NO. : 5,818,044
DATED : October 6, 1998
INVENTOR(S) : Lester Sodickson et al.

It is certified that error appears in the above-identified patent and that said Letters Patent is hereby corrected as shown below:

Column 8, line 1, replace "1—1" with --1-1--.

Column 20, line 22, replace "two or more" with --three or more--.

Signed and Sealed this

Ninth Day of November, 1999

Q. TODD DICKINSON

*Attest:*

*Attesting Officer*     *Acting Commissioner of Patents and Trademarks*